United States Patent [19]
Le Baut et al.

[11] Patent Number: 5,395,834
[45] Date of Patent: Mar. 7, 1995

[54] NEW BENZOPYRAN COMPOUNDS

[75] Inventors: Guillaume Le Baut, Saint Sebastien sur Loire; Jean-Paul Babingui; Sylvie Robert-Piessard, both of Nantes; Pierre Renard, Versailles; Daniel-Henri Caignard, Paris; Jean-Francois Renaud de la Faverie, Le Chesnay; Gérard Adam, Le Mesnil le Roi, all of France

[73] Assignee: Adir et Compagnie, Courbevoie, France

[21] Appl. No.: 225,532

[22] Filed: Apr. 11, 1994

Related U.S. Application Data

[62] Division of Ser. No. 117,301, Sep. 7, 1993.

[30] Foreign Application Priority Data

Sep. 9, 1992 [FR] France ................. 92 10741

[51] Int. Cl.⁶ ............... A61K 31/495; C07D 403/00; C07D 413/00
[52] U.S. Cl. ................. 514/253; 544/295; 544/367; 544/376
[58] Field of Search .............. 544/376; 514/253

[56] References Cited

U.S. PATENT DOCUMENTS 5,099,012 3/1992 Wu et al. ............... 536/17.5

FOREIGN PATENT DOCUMENTS 505017 9/1972 European Pat. Off. .
512899 11/1992 European Pat. Off. .

OTHER PUBLICATIONS

Ackland et al., Chem. Abst 118(23):233988y (1993).
Jacobsen et al., Chem. Abst. 117(23):233646q (1992).
Ohuchida et al., Chem Abst. 114(15):143143g (1990).
Matsuo et al., Chem. Abst. 114(9):81586t (1990).

*Primary Examiner*—Cecilia Tsang
*Attorney, Agent, or Firm*—Gordon W. Hueschen

[57] ABSTRACT

A compound selected from those of formula (I):

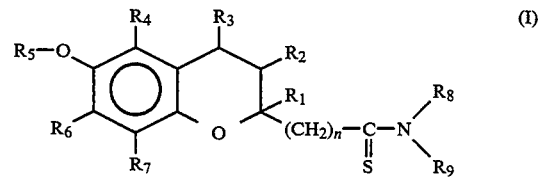

in which $R_1$, $R_2$, $R_3$, $R_4$, $R_5$, $R_6$, $R_7$, $R_8$, $R_9$ and n are as defined in the description, its optical isomers, and its addition salts thereof with a pharmaceutically-acceptable acid or base, and medicinal product containing the same for treating a mammal afflicted with a disorder connected with peroxydation processes and biosynthesis of eicosanoids.

7 Claims, No Drawings

NEW BENZOPYRAN COMPOUNDS

The present application is a division of our prior-filed copending application Ser. No. 08/117,301, filed Sep. 7, 1993.

The present invention relates to new benzopyran compounds.

Recently, Patent Application WO 88/08424 has described 2-chromanecarboxylic acid compounds and more generally (2-chromanyl)alkylcarboxylic acids.

It is henceforth established that lipid peroxidation is a major pathological factor. It is especially clear that the process of lipid peroxidation and the products which it generates can be harmful to cell viability.

The effects of lipid peroxidation have been implicated in many pathological conditions such as atherosclerosis, hemolytic anemias and damage due to ischemia/reperfusion (Oxidative Damage and Repair, Chemical, Biological and Medical Aspects, 1991 Pergamon Press, page XXi). The possibility of having available molecules which allow this lipid peroxidation phenomenon to be controlled thus proves to have great use for the clinician in preventing and treating pathologies involving such a phenomenon.

It is also known that the eicosanoids (prostaglandins and leukotrienes) resulting from the metabolism of arachidonic acid are the basis of the inflammatory mechanism. Compounds which make possible the inhibition of the activity of the enzymes lipoxygenase and/or cycloxygenase would thus be useful, for example in the prevention and treatment of rheumatoid arthritis, in asthma and in allergy.

The Applicant has now discovered new benzopyran thiocarboxamide compounds having an anti-oxidizing activity markedly better than those of the compounds which constitute the closest prior art.

The Applicant has also discovered that these new compounds made it possible to inhibit the synthesis of the eicosanoids as well as to preserve the intracellular pH when faced with acidosis. The compounds of the invention thus have an extremely advantageous action as cell protectors.

More specifically, the invention relates to new benzopyran compounds corresponding to the general formula (I):

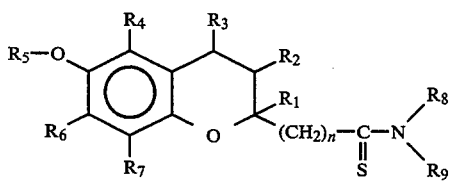

in which:

n represents an integer equal to 0 or 1, $R_1$, $R_2$, $R_3$, $R_4$, $R_6$ and $R_7$, which are identical or different, each represents independently of one another a hydrogen atom or a lower alkyl radical $R_a$—, where $R_a$ represents a linear or branched alkyl group containing 1 to 8 carbon atoms, $R_5$ represents:
a hydrogen atom,
a lower alkyl group $R_a$—,
a lower acyl group $R_a$—CO—,
an alkoxyalkyl group of form $R_a$—O—$R_b$—,
an alkoxycarbonyl group of form $R_a$—O—CO—,
an alkoxycarbonylalkyl group of form $R_a$—O—CO—$R_b$—,
a carboxyalkyl group of form HOOC—$R_a$—, where $R_a$ and $R_b$, which are identical or different, each represent, independently of one another, a linear or branched alkyl radical containing from 1 to 8 carbon atoms, $R_8$ and $R_9$
either form, together with the nitrogen atom which carries them, a group chosen from:
piperazine,
substituted piperazine,
piperidine,
substituted piperidine,
pyrrolidine,
substituted pyrrolidine,
morpholine,
morpholine substituted by one or a number of alkyl radicals,
tetrahydropyridine,
thiomorpholine,
azaspiran containing 5 to 12 members,
azaspiran containing 5 to 12 members which is substituted by one or a number of alkyl radicals or oxo groups,
mono- or bicyclic azacycloalkyl containing 7 to 12 members, optionally including in its skeleton from 1 to 2 additional hetero atoms chosen from oxygen, sulfur and nitrogen,
mono- or bicyclic azacycloalkyl containing 7 to 12 members, substituted by one or a number of alkyl radicals or oxo groups, optionally including 1 to 2 additional hetero atoms chosen from oxygen, sulfur and nitrogen,
a group —NH—$(CH_2)_k$—$NH_2$ in which k represents an integer equal to 2, 3 or 4,
and a substituted group —NH—$(CH_2)_k$—$NH_2$ in which k is as defined above,
it being understood that the term "substituted" affecting the above piperazine, piperidine, pyrrolidine and —NH—$(CH_2)_k$—$NH_2$ groups means that these groups can be substituted by one or a number of halogen atoms, hydroxyl radicals, carboxyl radicals, $R_{10}$ radicals, or radicals

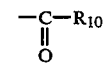

with $R_{10}$ being chosen from:
alkyl,
alkoxy,
alkenyl,
—$(CH_2)_n$—$R_{11}$ or

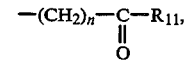

where n represents 0 or an integer from 1 to 5 and where $R_{11}$ represents a radical chosen from phenyl, benzhydryl, 1,1-diphenylmethylidenyl, thienyl, pyrrolyl, pyrrolidinyl, furyl, pyrimidinyl, pyridyl, benzodioxolyl, benzodioxanyl, naphthyl, quinolyl, isoquinolyl, cycloalkyl and dicycloalkylmethyl; the term "cycloalkyl" representing a mono- or bicyclic group containing 3 to 12 members, it being possible for these radicals $R_{10}$ themselves to be substituted by one or a number of radicals chosen from halogen, trifluoromethyl, oxo, carboxyl, hydroxyl, alkyl, alkoxy, haloalkoxy, acetyl and pyrrolidinyl, or $R_8$ and $R_9$, which are identical or different, each represent, independently of one another:

a hydrogen atom, a lower alkyl group $R_a$— or a substituted lower alkyl group $R_a$—, a lower alkenyl group or a substituted lower alkenyl group, where the alkenyl group represents a linear or branched unsaturated hydrocarbon comprising 2 to 8 carbon atoms, a group A—$(CH_2)_m$— or a substituted group A—$(CH_2)_m$—, where m is an integer equal to 0, 1 or 2 and A represents a cycloalkyl group comprising p carbon atoms with p being an integer from 3 to 7, an alkoxyalkyl group of form $R_a$—O—$R_b$— or a substituted alkoxyalkyl group of form $R_a$—O—$R_b$— where $R_a$ and $R_b$, which are identical or different, represent a linear or branched lower alkyl radical containing 1 to 8 carbon atoms, an alkoxycarbonylalkyl group of form $R_a$—O—CO—$R_b$— or a substituted alkoxycarbonylalkyl group of form $R_a$—O—CO—$R_b$—, with $R_a$ and $R_b$ as defined above, a group B—$(CH_2)_q$— or a substituted group B—$(CH_2)_q$—, where q is an integer equal to 0, 1, 2 or 3 and B represents a naphthalene, 1,3-dioxane, pyran or benzopyran radical, a group E—$(CH_2)_q$— or a substituted group E—$(CH_2)_q$—, with q as defined above and E representing a substituted or unsubstituted azaspiran or azacycloalkyl group, as defined above, a phenyl—$(CH_2)_q$— group or a substituted phenyl$(CH_2)_q$— group, with q as defined above, a heteroaryl—$(CH_2)_q$— group or a substituted heteroaryl—$(CH_2)_q$— group, with q as defined above and where the heteroaryl is chosen from: furan, quinoline, isoquinoline, pyridine, thiophene, thiazole, isothiazole, oxazole, isoxazole, naphthyridine, benzofuran, β-carboline, or γ-carboline, a guanidino or amidino group which is unsubstituted or substituted by one or a number of linear or branched alkyl groups containing 1 to 6 carbon atoms, or one of the following radicals $D_1$ to $D_4$:

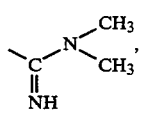
D1

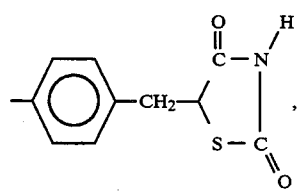
D2

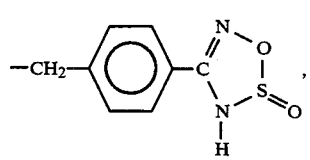
D3

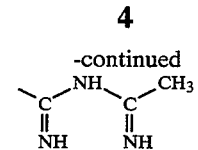
D4 it being understood that during this description of the general formula (I), the term "substituted" affecting the groups as previously defined: lower alkyl $R_a$—, lower alkenyl, A—$(CH_2)_m$—, alkoxyalkyl $R_a$—O—$R_b$—, alkoxycarbonylalkyl $R_a$—O—CO—$R_b$—, B—$(CH_2)_q$—, phenyl—$(CH_2)_q$—, heteroaryl—$(CH_2)_q$—, means, when this is not specified, that these groups can be substituted by one or a number of identical or different radicals and each representing, independently of one another:

a lower alkyl group $R_c$—, lower alkoxy $R_c$—O—, lower acyl $R_c$—CO—, triftuoromethyl, carboxyl, hydroxyl, oxo, guanidino, amidino, or a halogen atom, where $R_c$ represents a linear or branched alkyl group containing 1 to 6 carbon atoms, to their optical isomers, in the pure form or in the form of mixtures, as well as, if appropriate, to their addition salts with a pharmaceutically acceptable acid or base.

Among the pharmaceutically acceptable acids or bases which can be used to salify the compounds of the invention, there may be mentioned, by way of examples and in a non-limiting way, hydrochloric, hydrobromic, sulfuric, nitric, oxalic, malic, maleic, succinic, tartaric methanesulfonic, camphoric or camphosulfonic acid, sodiuhydroxide, potassium hydroxide, triethylamine, diethylamine, ethanolamine, arginine, lysine and diethanolamine.

The invention applies to the process for obtaining the compounds of formula (I), characterized in that there is used, as starting material, a compound of formula (II):

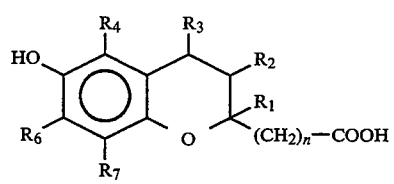
(II)

with $R_1$, $R_2$, $R_3$, $R_4$, $R_6$, $R_7$ and n having the same meaning as in the general formula (I), which can be esterified, in anhydrous basic medium, with a compound $R_5''$—Hal or $R_5''$—O—$R_5''$, where Hal represents a halogen atom and where $R_5''$ represents a lower acyl group $R_a$—CO— in which $R_a$ is as defined in the formula (I), to produce a compound of formula (III):

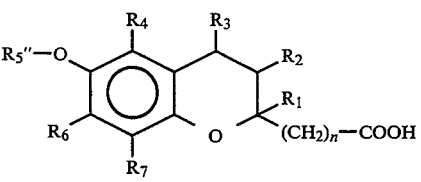
(III)

with $R_1$, $R_2$, $R_3$, $R_4$, $R_6$, $R_7$, n, and $R_5''$ as defined above, which is converted to its halide by reacting with a halogenating agent, and then treated, in a suitable solvent, in the presence of an alkaline agent, with an amine of formula (IV):

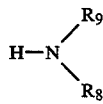

(IV)

with $R_8$ and $R_9$ having the same meaning as in the formula (I), to produce a compound of formula ($I_a$):

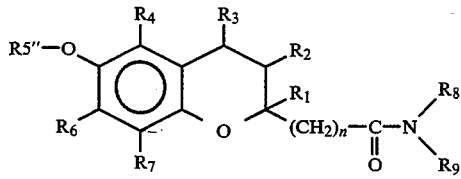

($I_a$)

with $R_1$, $R_2$, $R_3$, $R_4$, $R_6$, $R_7$, $R_8$, $R_9$, n, and $R_5''$ as defined above, which can then, be saponified by reacting with an alkali metal or alkaline-earth metal hydroxide to a compound of formula ($I_b$):

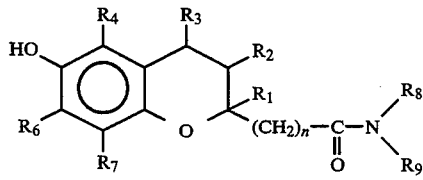

($I_b$)

with $R_1$, $R_2$, $R_3$, $R_4$, $R_6$, $R_7$, $R_8$, $R_9$ and n as defined above, then, if appropriate, etherified by reacting with a derivative of formula $R_5'''$—O—$R_5'''$ or $R_5'''$—Hal', where Hal' represents a halogen atom and $R_5'''$ represents a lower alkyl group $R_a$, a lower acyl group $R_a$—CO—, an alkoxyalkyl group of form $R_a$—O—$R_b$—, an alkoxycarbonyl group of form $R_a$—O—CO—, an alkoxycarbonylalkyl group of form $R_a$—O—CO—$R_b$—, or a carboxyalkyl group of form HOOC—$R_a$—, with $R_a$ and $R_b$ as defined in the formula (I), to produce a compound of formula ($I_c$):

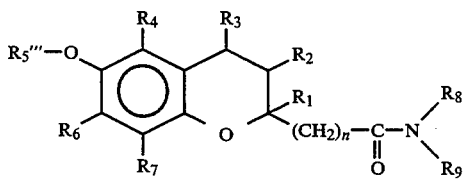

($I_c$)

with $R_1$, $R_2$, $R_3$, $R_4$, $R_6$, $R_7$, $R_8$, $R_9$, n, and $R_5'''$ as defined above, which compounds of formula ($I_a$), ($I_b$) and ($I_c$) are then subjected to the action of Lawesson's reagent to produce the corresponding compounds of formula (I), it being possible for the compounds of formula (I) to be, if desired:

purified, separated into their optical isomers, in the pure form or in the form of mixtures, or converted to their addition salts with a pharmaceutically acceptable base or acid.

The invention also applies to the process for obtaining the compounds of formula (I'):

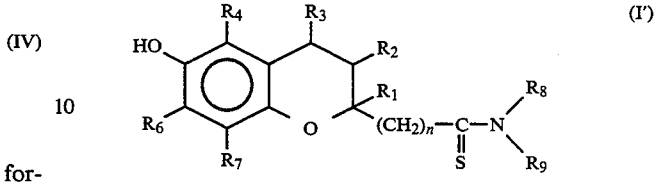

(I')

in which $R_1$, $R_2$, $R_3$, $R_4$, $R_6$, $R_7$, $R_8$, $R_9$ and n are as defined in the formula (I), a specific case of the compounds of formula (I) in which $R_5$ represents a hydrogen atom, and compounds of formula ($I'_a$) of formula:

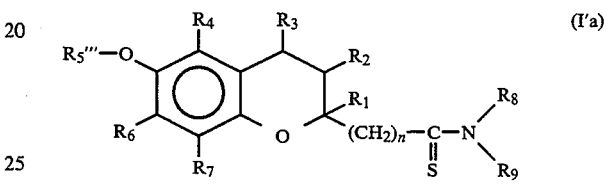

($I'_a$)

in which $R_1$, $R_2$, $R_3$, $R_4$, $R_6$, $R_7$, $R_8$, $R_9$ and n are as defined in the formula I and $R_5'''$ is as defined above, a specific case of the compounds of formula (I) in which $R_5$ represents a radical $R_5'''$, characterized in that a compound of formula (I''):

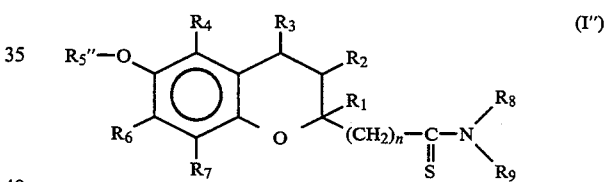

(I'')

in which $R_1$, $R_2$, $R_3$, $R_4$, $R_6$, $R_7$, $R_8$, $R_9$ and n are as defined above and $R_5''$ represents a lower acyl group $R_a$—CO— in which $R_a$ is as defined in the formula (I), a specific case of the compounds of formula (I) in which $R_5$ represents a radical $R_5''$, is saponified by reacting with an alkali metal or alkaline-earth metal hydroxide, to produce the corresponding compound of formula (I'), which is etherified or esterified, if appropriate, by reacting with a compound of formula $R_5'''$—O—$R_5'''$ or $R_5'''$—Hal'', where Hal'' represents a halogen atom and $R_5'''$ is as defined above, to produce the corresponding compound of formula ($I'_a$), which compounds of formula (I') and ($I'_a$) can be, if desired:

purified, separated into their optical isomers, in the pure form or in the form of mixtures, or converted to their addition salts with a pharmaceutically acceptable acid or base.

Compared with the compounds of the prior art, the compounds of the present invention surprisingly have very significant antioxidizing properties. Pharmacological studies have especially shown that these compounds possessed notable protective activities in the context of peroxidation processes of cell lipids and of low density lipoproteins (LDL). These activities are, for some of the compounds of the invention, 100 times greater than that of the closest compound of the prior art, that is to say Example 102 of Application WO 88/08424. (Pharmacological Examples B and C of the present Application).

Moreover, certain compounds of the present invention have the distinctive characteristic of having a powerful inhibiting effect on the biosynthesis of eicosanoids, which result from peroxidized compounds, potential free radical generators, an inhibiting effect which the closest compound of the prior art does not have.

Additionally, the Applicant has discovered that the compounds of the invention were excellent protectors of intracellular pH when faced with intracellular acidification, one of the main causes of tissue ischemia. In effect, the compounds of the invention are shown to be powerful inhibitors of bicarbonate carriers and especially of the sodium-independent $Cl^-/HCO_3^-$ exchanger of cultured heart cells (cardiocytes). (Pharmacological Example D of the present Application). The escape of bicarbonate out of the cell is thus halted and makes possible the neutralization of cell acidification and of the ionic and metabolic traumas which are associated with it.

The compounds of the present invention can thus be used in the treatment or prevention of central or peripheral ischemic disorders, inflammatory diseases, rheumatoid arthritis, metabolic diseases, atheroma, arteriosclerosis, respiratory diseases, asthma, emphysema, diseases of immunological origin, lupus erythematosus, allergic reactions, cerebral or cutaneous aging as well as in the prevention and treatment of damage due to surgical traumas such as organ reperfusion.

Another subject of the present invention is the pharmaceutical compositions containing a compound of formula (I), or one of its addition salts with a pharmaceutically acceptable acid or base, in combination with one or a number of pharmacologically acceptable excipients.

Among the pharmaceutical compositions according to the invention, there can more particularly be mentioned those which are suitable for oral, percutaneous, cutaneous, parenteral, nasal, rectal, perlingual, ocular or pulmonary administration and especially injectable or drinkable preparations, aerosols, eye or nose drops, simple, film-coated or sugar-coated tablets, capsules, including hard gelatin capsules, creams, ointments, dermal gels, pills, packets, sachets, granules and suppositories.

The dose varies according to the age, weight and sex of the patient, the route of administration, the nature and intensity of the ailment, and according to the possible associated treatments. The doses range from 0.5 mg to 1 g per day, particularly from 0.5 mg to 100 mg per day, for example from 10 mg to 100 mg per day.

The examples which follow illustrate the invention but do not limit it in any way.

The starting materials are described in the literature or are easily accessible to the person skilled in the art.

The infrared spectra are produced in potassium bromide disks containing approximately 1% of the product to be analysed.

EXAMPLE 1:
N-phenyl-6-acetoxy-3,4-dihydro-2,5,7,8-tetramethyl-2H-1-benzopyran-2-thiocarboxamide Stage A:
6-Acetoxy-3,4-dihydro-2,5,7,8-tetramethyl-2H-1-benzopyran-2-carboxylic acid 50 gram (0.2 mol) of 6-hydroxy-3,4-dihydro-2,5,7,8-tetramethyl-2H-1-benzopyran-2-[1])carboxylicacid (or (6-hydroxy-3,4-dihydro-2,5,7,8-tetramethyl-2H[1]benzopyran-2-yl)carboxylic acid) are dissolved in 150 cm³ of anhydrous pyridine. 9.4 cm³ (0.1 mol) of acetic acid are added dropwise under a nitrogen stream. The mixture is stirred for 2 h at a temperature of 30° C. After cooling, the mixture is poured onto ice, the expected product is extracted with ethyl ether, the organic phase is washed with a 0.2N hydrochloric acid solution and then with water to neutrality. After evaporating the solvent, an oily mass is collected which crystallizes after trituration in diisopropyl ether.

Stage B:
N-Phenyl-6-acetoxy-3,4-dihydro-2,5,7,8-tetramethyl-2H-1-benzopyran-2-carboxamide 3.25 g (11.1 mol) of the compound obtained in the preceding stage and 40 cm³ of anhydrous benzene are introduced into a round-bottomed flask. After dissolution, 1.2 cm³ of thionyl chloride are added. The mixture is heated at reflux for 3 h and left to cool. The solvent is driven off under vacuum. The residue is taken up in 30 cm³ of anhydrous benzene, and again the solvent is evaporated so as to remove the excess thionyl chloride. The acid chloride thus obtained is dissolved in 20 cm³ of dichloroethane. Moreover, 1.04 g (11.1 mmol) of aniline and 4.7 cm³ of triethylamine are dissolved in 20 cm³ of dichloroethane. The acid chloride solution is poured dropwise onto this mixture. The mixture is left to stir at ordinary temperature for 2 h. The solvent is driven off under vacuum. The residue is taken up in 30 cm³ of water and neutralized with a saturated sodium bicarbonate solution. The product is extracted with dichloromethane. The organic phase is washed with water and then dried over anhydrous sodium sulfate. After removal of the solvent, the product is purified by passing through a column of silica gel, eluting with isopropyl ether. Mass of the product obtained: 3.3 g.

Yield: 80.9%

Melting point: 104°–105° C.

Infrared spectral characteristics:

| | |
|---|---|
| $\nu$ C=O: | 1750 cm$^{-1}$ |
| $\nu$ C=O (amide): | 1685 cm$^{-1}$ |
| $\nu$ C=C: | 1595 cm$^{-1}$ |
| $\nu$ SNH: | 1520 cm$^{-1}$. |

Stage C:
N-Phenyl-6-acetoxy-3,4-dihydro-2,5,7,8-tetramethyl-2H-1-benzopyran-2-thiocarboxamide 5.54 g (17 mmol) of N-phenyl-6-acetoxy-3,4-dihydro-2,5,7,8-tetramethyl-2H-1-benzopyran-2-carboxamide, obtained in the preceding stage, are dissolved in 125 cm³ of anhydrous toluene. 4.15 g (10.2 mmol) of Lawesson's reagent are added and then the mixture is heated at reflux for 6 hours. The solvent is evaporated and the title compound is purified on a column of silica gel, eluting with dichloromethane. There is obtained a yellow crystalline powder which is crystallized from diisopropyl ether.

Yield 90 %

EXAMPLE 2:
N-phenyl-6-hydroxy-3,4-dihydro-2,5,7,8-tetramethyl-2H-1-benzopyran-2-thiocarboxamide In a two-necked, round-bottomed flask, 2.75 g (7.48 mmol) of the compound obtained in Stage B of Example 1 are dissolved in 60 cm$^3$ of 80% ethanol. Under a nitrogen stream, 18 cm$^3$ of 2.5N sodium hydroxide are added. The mixture is left to stir at ordinary temperature for 2 h. The mixture is diluted with water, acidified with acetic acid and then the product is extracted with dichloromethane. The organic phase is washed with water and then dried. The mixture is purified by passing through a column of silica gel, eluting with isopropyl ether to obtain N-phenyl-6-hydroxy-3,4-dihydro-2,5,7,8-tetramethyl-2H-1-benzopyran-2-carboxamide (yield: 86%; melting point: 107°–109° C.) and then the reaction is carried out as in Stage C of Example 1, replacing N-phenyl-6-acetoxy-3,4-dihydro-2,5,7,8-tetramethyl-2H-1-benzopyran-2-carboxamide with N-phenyl-6-hydroxy-3,4-dihydro-2,5,7,8-tetramethyl-2H-1-benzopyran-2-carboxamide.

Yield: 34%
Melting point: 150°–152° C. (diisopropyl ether)
Infrared spectral characteristics:
$\nu$ OH: 3500 cm$^{-1}$
$\nu$ NH: 3320 cm$^{-1}$
$\nu$ C=S: 720 cm$^{-1}$.

2nd process:

5.74 mmol of the compound of Example 1 are dissolved in 80 cm$^3$ of 60% ethanol and, under nitrogen, 14 cm$^3$ of 2.5N sodium hydroxide are added. The mixture is stirred for 3 h, then diluted with water and acidified with acetic acid. The product is extracted with dichloromethane, the organic phase is washed with water, dried over anhydrous sodium sulfate and then the solvent is evaporated. The oil obtained is taken up in 15 cm$^3$ of isopropyl ether and the product is isolated by using the conventional techniques of chromatographic or crystallographic separation.

The title product is obtained:
Yield: 89%
Melting point: 150°–152° C.
Solvent: diisopropyl ether.

EXAMPLE 3:
N-(2,4,5-trimethylphenyl)-6-acetoxy-3,4-dihydro-2,5,7,8-tetramethyl-2H-1-benzopyran-2-thiocarboxamide The title product is obtained by replacing aniline Stage B of Example 1 with 2,4,5-trimethylaniline.

EXAMPLE 4:
N-(2,4,5-trimethylphenyl)-6-hydroxy-3,4-dihydro-2,5,7,8-tetramethyl-2H-1-benzopyran-2-thiocarboxamide By carrying out the reaction as in Example 2, but using N-(2,4,5-trimethylphenyl)-6-acetoxy-3,4-dihydro-2,5,7,8-tetramethyl-2H-1-benzopyran-2-carboxamide (melting point: 160°–162° C.), the title compound is obtained:

Melting point: 124°–125° C. (diisopropyl ether)
Infrared spectral characteristics:

| $\nu$ NH: | 3320 cm$^{-1}$ |
| $\nu$ OH: | 3450 cm$^{-1}$ |
| $\nu$ C=S: | 1165 cm$^{-1}$. |

EXAMPLE 5:
N-(4,6-dimethylpyrid-2-yl)-6-acetoxy-3,4-dihydro-2,5,7,8-tetramethyl-2H-1-benzopyran-2-thiocarboxamide The title product is obtained by replacing aniline in Stage B of Example 1 with 2-amino-4,6-dimethylpyridine.

EXAMPLE 6:
N-(4,6-dimethylpyrid-2-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 5, the title product is obtained Yield: 60%
Melting point: 180°–190° C. (diisopropyl ether)
Infrared spectral characteristics:

| $\nu$ (OH): | 3420 cm$^{-1}$ |
| $\nu$ (NH): | 3310 cm$^{-1}$ |
| $\nu$ (C=C, N=C): | 1620, 1570 cm$^{-1}$. |

EXAMPLE 7:
N-(3,4,5-trimethoxyphenyl)-6-acetoxy-3,4-dihydro-2,5,7,8-tetramethyl-2H-1-benzopyran-2-thiocarboxamide The title product is obtained by replacing aniline in Stage B of Example 1 with 3,4,5-trimethoxyaniline.

EXAMPLE 8:
N-(3,4,5-trimethoxyphenyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 7, the title product is obtained:

Yield: 82%
Melting point: 147°–148° C. (diisopropyl ether)
Infrared spectral characteristics:
$\nu$ OH: 3460 cm$^{-1}$
$\nu$ NH: 3320 cm$^{-1}$.

EXAMPLE 9:
N-hexyl-N-(4,6-dimethylpyrid-2-yl)-6-acetoxy-3,4-dihydro-2,5,7,8-tetramethyl-2H-1-benzopyran-2-thiocarboxamide The title product is obtained by replacing aniline in Stage B of Example 1 with N-(4,6-dimethylpyrid-2-yl)hexylamine.

EXAMPLE 10:
N-hexyl-N-(4,6-dimethylpyrid-2-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 9, the title product is obtained.

EXAMPLE 11:
N-phenyl-N-(buten-3-yl)-6-acetoxy-3,4-dihydro-2,5,7,8-tetramethyl-2H-1-benzopyran-2-thiocarboxamide The title product is obtained by replacing aniline in Stage B of Example 1 with N-(buten-3-yl)aniline.

EXAMPLE 12:
N-phenyl-N-(buten-3-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 11, the title product is obtained.

EXAMPLE 13:
N-furfuryl-6-acetoxy-3,4-dihydro-2,5,7,8-tetramethyl-2H-1-benzopyran-2-thiocarboxamide The title product is obtained by replacing aniline in Stage B of Example 1 with furfurylamine.

EXAMPLE 14:
N-furfuryl-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 13, the title product is obtained.

EXAMPLE 15:
N-(4-hydroxy-2,3-dimethylphenyl)-6-acetoxy-3,4-dihydro-2,5,7,8-tetramethyl-2H-1-benzopyran-2-thiocarboxamide The title product is obtained by replacing aniline in Stage B of Example 1 with 4-hydroxy-2,3-dimethylaniline.

EXAMPLE 16:
N-(4-hydroxy-2,3-dimethylphenyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 15, the title product is obtained.

EXAMPLE 17:
N-(5,7-dimethylnaphthyridin-2-yl)-6-acetoxy-3,4-dihydro-2,5,7,8-tetramethyl-2H-1-benzopyran-2-thiocarboxamide The title product is obtained by replacing aniline in Stage B of Example 1 with 2-amino-5,7-dimethylnaphthyridine.

EXAMPLE 18:
N-(5,7-dimethylnaphthyridin-2-yl)-6-hydroxy-3,4-dihydro-2,5,7,8-tetramethyl-2H-1-benzopyran-2-thiocarboxamide By carrying out the reaction as in Example 2 (2nd process), but replacing the compound of Exampls 1 with the compound of Example 17, the title product is obtained.

EXAMPLE 19:
N-cyclopropylmethyl-N-(4,6-dimethylpyrid-2-yl)-6-acetoxy-3,4-dihydro-2,5,7,8-tetramethyl-2H-1-benzopyran-2-thiocarboxamide The title product is obtained by replacing aniline in Stage B of Example 1 with N-(4,6-dimethylpyrid-2-yl)cyclopropylmethylamine and by changing the duration of the heating stage at reflux from 3 hours to 4 hours.

EXAMPLE 20:
N-cyclopropylmethyl-N-(4,6-dimethylpyrid-2-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 19, the title product is obtained.

EXAMPLE 21:
N-(4-methylquinol-2-yl)-6-acetoxy-3,4-dihydro-2,5,7,8-tetramethyl-2H-1-benzopyran-2-thiocarboxamide The title product is obtained by replacing aniline in Stage B of Example 1 with 2-amino-4-methylquinoline.

EXAMPLE 22:
N-(4-methylquinol-2-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 21, the title product is obtained.

EXAMPLE 23:
N-isobutyl-N-(4,6-dimethylpyrid-2-yl)-6-acetoxy-3,4-dihydro-2,5,7,8-tetramethyl-2H-1-benzopyran-2-thiocarboxamide The title product is obtained by replacing aniline in Stage B of Example 1 with N-(4,6-dimethylpyrid-2-yl)isobutylamine.

EXAMPLE 24:
N-isobutyl-N-(4,6-dimethylpyrid-2-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 23, the title product is obtained.

EXAMPLE 25:
N-(2,6-dimethylphenyl)-6-acetoxy-3,4-dihydro-2,5,7,8-tetramethyl-2H-1-benzopyran-2-thiocarboxamide The title product is obtained by replacing aniline in Stage B of Example 1 with 2,6-dimethylaniline.

EXAMPLE 26:
N-(2,6-dimethylphenyl)-6-hydroxy-3,4-dihydro-2,5,7,8-tetramethyl-2H-1-benzopyran-2-thiocarboxamide By carrying out the reaction as in Example 2, but using N-(2,6-dimethylphenyl)-6-acetoxy-3,4-dihydro-2,5,7,8-tetramethyl-2H-1-benzopyran-2-carboxamide, the title product is obtained.

Melting point: 122°–123° C. (diisopropyl ether)
Infrared spectral characteristics:
$\nu$ OH: 3400 cm$^{-1}$
$\nu$ NH: 3320 cm$^{-1}$ ν C=S: 1040 cm⁻¹.

EXAMPLE 27:
N-(2-carboxy-4,5-dimethoxyphenyl)-6-acetoxy-3,4-dihydro-2,5,7,8-tetramethyl-2H-1-benzopyran-2-thiocarboxamide The title product is obtained by replacing aniline in Stage B of Example 1 with 2-carboxy-4,5-dimethoxyaniline.

EXAMPLE 28:
N-(2-carboxy-4,5-dimethoxyphenyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 27, the title product is obtained.

EXAMPLE 29:
N-(3,5-dichloro-4-hydroxyphenyl)-6-acetoxy-3,4-dihydro-2,5,7,8-tetramethyl-2H-1-benzopyran-2-thiocarboxamide The title product is obtained by replacing aniline in Stage B of Example 1 with 3,5-dichloro-4-hydroxyaniline.

EXAMPLE 30:
N-(3,5-dichloro-4-hydroxyphenyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 29, the title product is obtained.

EXAMPLE 31:
N-(2-carboxy-4,6-dimethylphenyl)-6-acetoxy-3,4-dihydro-2,5,7,8-tetramethyl-2H-1-benzopyran-2-thiocarboxamide The title product is obtained by replacing aniline in Stage B of Example 1 with 2-carboxy-4,5-dimethylaniline.

EXAMPLE 32:
N-(2-carboxy-4,6-dimethylphenyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 31, the title product is obtained.

EXAMPLE 33:
N-(2,4,6-trimethylphenyl)-6-acetoxy-3,4-dihydro-2,5,7,8-tetramethyl-2H-1-benzopyran-2-thiocarboxamide The title product is obtained by replacing aniline in Stage B of Example 1 with 2,4,6-trimethylaniline.

EXAMPLE 34:
N-(2,4,6-trimethylphenyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 33, the title product is obtained.

EXAMPLE 35:
N-(2-methylquinol-4-yl)-6-acetoxy-3,4-dihydro-2,5,7,8-tetramethyl-2H-1-benzopyran-2-thiocarboxamide The title product is obtained by replacing aniline in Stage B of Example 1 with 4-amino-2-methylquinoline.

EXAMPLE 36:
N-(2-methylquinol-4-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 35, the title product is obtained.

EXAMPLE 37:
1-oxa-2-oxo-3,8-diaza-8-(6-acetoxy-3,4-dihydro-2,5,7,8-tetramethyl-2H-1-benzopyran-2-thiocarbonyl)spiro[4.5] decane The title product is obtained by replacing aniline in Stage B of Example 1 with 1-oxa-2-oxo-3,8-diazaspiro[4.5]decane.

EXAMPLE 38:
1-oxa-2-oxo-3,8-diaza-8-((6-hydroxy-3,4-dihydro-2,5,7,8-tetramethyl-2H-1-benzopyran-2-yl)thiocarbonyl)spiro[4.5] decane By carrying out the reaction as in Example 2 (2nd process), but replacing the compound of Example 1 with the compound of Example 37, the title product is obtained.

EXAMPLE 39:
N-(4-chloro-1-naphthyl)-6-acetoxy-3,4-dihydro-2,5,7,8-tetramethyl-2H-1-benzopyran-2-thiocarboxamide The title product is obtained by replacing aniline in Stage B of Example 1 with 1-amino-4-chloronaphthalene.

EXAMPLE 40:
N-(4-chloro-1-naphthyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 39, the title product is obtained.

EXAMPLE 41:
N-(2-naphthyl)-6-acetoxy-3,4-dihydro-2,5,7,8-tetramethyl-2H-1-benzopyran-2-thiocarboxamide The title product is obtained by replacing aniline in Stage B of Example 1 with 2-aminonaphthalene.

EXAMPLE 42:
N-(2-naphthyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 41, the title product is obtained.

EXAMPLE 43:
N-(isoquinol-5-yl)-6-acetoxy-3,4-dihydro-2,5,7,8-tetramethyl-2H-1-benzopyran-2-thiocarboxamide The title product is obtained by replacing aniline in Stage B of Example 1 with 5-aminoisoquinoline.

EXAMPLE 44:
N-(isoquinol-5-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 43, the title product is obtained.

EXAMPLE 45:
N-(thiazol-2-yl)-6-acetoxy-3,4-dihydro-2,5,7,8-tetramethyl-2H-1-benzopyran-2-thiocarboxamide The title product is obtained by replacing aniline in Stage B of Example 1 with 2-aminothiazole.

EXAMPLE 46:
N-(thiazol-2-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 45, the title product is obtained.

EXAMPLE 47:
N-{4-[(2,4-dioxo-5-thiazolidinyl)methyl]-phenyl}-6-acetoxy-3,4-dihydro-2,5,7,8-tetramethyl-2H-1-benzopyran-2-thiocarboxamide The title product is obtained by replacing aniline in Stage B of Example 1 with N-{4-[(2,4-dioxo-5-thiazolidinyl)methyl]phenyl}amine.

EXAMPLE 48:
N-{4-[(2,4-dioxo-5-thiazolidinyl)methyl]-phenyl}-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 47, the title product is obtained.

EXAMPLE 49:
N-((thien-2-yl)methyl)-6-acetoxy-3,4-dihydro-2,5,7,8-tetramethyl-2H-1-benzopyran-2-thiocarboxamide The title product is obtained by replacing aniline in Stage B of Example 1 with 2-thiophenemethylamine.

EXAMPLE 50:
N-((thien-2-yl)methyl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 49, the title product is obtained.

EXAMPLE 51:
N-butyl-N-phenyl-6-acetoxy-3,4-dihydro-2,5,7,8-tetramethyl-2H-1-benzopyran-2-thiocarboxamide The title product is obtained by replacing aniline in Stage B of Example 1 with N-butylaniline.

EXAMPLE 52: N-butyl-N-phenyl-6-hydroxy-3,4-dihydro-2,5,7,8-tetr-methyl-2H-1-benzopyran-2-thiocarboxamide By carrying out the reaction as in Example 2 (2nd process), but replacing the compound of Example 1 with the compound of Example 51, the title product is obtained.

EXAMPLES 53 TO 62

The following products are likewise obtained by following Examples 1 and 2 and by using the appropriate amines:

EXAMPLE 53:
N-methoxyethyl-6-acetoxy-3,4-dihydro-2,5,7,8-tetramethyl-2H-1-benzopyran-2-thiocarboxamide

EXAMPLE 54:
N-methoxyethyl-6-hydroxy-3,4-dihydro-2,5,7,8-tetramethyl-2H-1-benzopyran-2-thiocarboxamide

EXAMPLE 55:
N-phenyl-N-ethoxycarbonylmethyl-6-acetoxy-3,4-dihydro-2,5,7,8-tetramethyl-2H-1-benzopyran-2-thiocarboxamide

EXAMPLE 56:
N-Phenyl-N-ethoxycarbonylmethyl-6-hydroxy-3,4-dihydro-2,5,7,8-tetramethyl-2H-1-benzopyran-2-thiocarboxamide

EXAMPLE 57:
N-guanidino-6-acetoxy-3,4-dihydro-2,5,7,8-tetramethyl-2H-1-benzopyran-2-thiocarboxamide

EXAMPLE 58:
N-guanidino-6-hydroxy-3,4-dihydro-2,5,7,8-tetramethyl-2H-1-benzopyran-2-thiocarboxamide

EXAMPLE 59:
1-((6-acetoxy-3,4-dihydro-2,5,7,8-tetramethyl-2H-1-benzopyran-2-yl) thiocarbonyl)-3,3-dimethylguanidine

EXAMPLE 60:
1-((6-hydroxy-3,4-dihydro-2,5,7,8-tetramethyl-2H-1-benzopyran -2-yl)thiocarbonyl)-3,3-dimethylguanidine

EXAMPLE 61:
N-{4-[(2-oxo-1,2,3,5-oxathiadiazol-4-yl)-methyl]-phenyl}-6-acetoxy-3,4-dihydro-2,5,7,8-tetramethyl-2H-1-benzopyran-2-thiocarboxamide

EXAMPLE 62:
N-{4-[(2-oxo-1,2,3,5-oxathiadiazol-4-yl)-methyl]-phenyl}-6-hydroxy-3,4-dihydro-2,5,7,8-tetramethyl-2H-1-benzopyran-2-thiocarboxamide

EXAMPLE 63:
N-(1,3-dihydroxy-2-methyl-2-propyl)-6-acetoxy-3,4-dihydro-2,5,7,8-tetramethyl-2H-1-benzopyran-2-thiocarboxamide The title product is obtained by replacing aniline in Stage B of Example 1 with 2-amino-2-methyl-1,3-propanediol.

EXAMPLE 64:
N-(2,2,5-trimethyl-1,3-dioxan-5-yl)-6-acetoxy-3,4-dihydro-2,5,7,8-tetramethyl-2H-1-benzopyran-2-thiocarboxamide 3 grams (7.9 mmol) of the compound of Example 63 are dissolved in 45 cm$^3$ of 2,2-dimethoxypropane, 15 cm$^3$ of anhydrous dimethylformamide and then 60 milligrams of para-toluenesulfonic acid are added. The mixture is heated at reflux for one hour. The excess 2,2-dimethoxypropane is evaporated under vacuum. The residual mixture is diluted with water. The product is extracted with dichloromethane. The organic phase is washed with a sodium bicarbonate solution and then with water. The title compound is purified by passing through a column of silica gel, eiuting with ethyl ether. The title product is obtained.

EXAMPLE 65:
N-(2,2,5-trimethyl-1,3-dioxan-5-yl)-6-hydroxy-3,4-dihydro-2,5,7,8-tetramethyl-2H-1-benzopyran-2-thiocarboxamide By carrying out the reaction as in Example 2 (2nd process), but replacing the compound of Example 1 with the compound of Example 64, the title product is obtained.

EXAMPLE 66:
N-(4,6-dimethylpyrid-2-yl)-6-methoxymethoxy-3,4-dihydro-2,5,7,8-tetramethyl-2H-1-benzopyran-2-thiocarboxamide

Stage A:
6-methoxymethoxy-3,4-dihydro-2,5,7,8-tetramethyl-2H-1-benzopyran-2-carboxylic acid 50 grams (0.2 mol) of 6-hydroxy-3,4-dihydro-2,5,7,8-tetramethyl-2H-1-benzopyran-2-carboxylic acid are dissolved in 150 cm$^3$ of anhydrous pyridine. 16.34 cm$^3$ (0.2 mol) of bromomethyl methyl ether are added dropwise. The mixture is stirred for 2 hours and then the solution is poured onto ice. The mixture is acidified with acetic acid and then extracted with methylene chloride. The organic phase is washed with water and dried over anhydrous sodium sulfate, then the title product is purified by passing through a column of silica gel, eluting with methylene chloride.

Stage B:
N-(4,6-dimethylpyrid-2-yl)-6-methoxymethoxy-3,4-dihydro-2,5,7,8-tetramethyl-2H-1-benzopyran-2-carboxamide 5.4 grams (18.47 mmol) of the compound of the preceding stage are dissolved in 30 cm$^3$ of anhydrous benzene, 2.2 cm$^3$ (27.41 mmol) of thionyl chloride are added, the mixture is heated at reflux for 3 hours and the solvent is driven off under vacuum in removing the excess thionyl chloride. The acid chloride thus obtained is dissolved in 30 cm$^3$ of dichloroethane. 2.26 grams (18.5 mmol) of 2-amino-4,6-dimethylpyridine are dissolved in 20 cm$^3$ of dichloroethane in another receptacle, 7.7 cm$^3$ of triethylamine are added and the above acid chloride solution is poured dropwise into this mixture. After stirring for 8 hours, the solvent is evaporated under vacuum, the residue is taken up in 30 cm$^3$ of water, neutralized with a NaHCO$_3$ solution, extracted with methylene chloride, the organic phase is washed with water and then dried over sodium sulfate. After evaporation of the solvent, the mixture is purified by chromatography on silica gel, eluting with methylene chloride.

Stage C:
N-(4,6-dimethylpyrid-2-yl)-6-methoxymethoxy-3,4-dihydro-2,5,7,8-tetramethyl-2H-1-benzopyran-2-thiocarboxamide By carrying out the reaction as in Stage C of Example 1, but replacing N-phenyl-6-acetoxy-3,4-dihydro-2,5,7,8-tetramethyl-2H-1-benzopyran-2-thiocarboxamide with the compound obtained in the above Stage B, the title compound is obtained.

EXAMPLE 67:
N-(4,6-dimethylpyrid-2-yl)-6-ethoxycarbonylmethoxy-3,4-dihydro-2,5,7,8-tetramethyl-2H-1-benzopyran-2-thiocarboxamide By carrying out the reaction as in Example 66, but replacing the bromomethyl methyl ether of Stage A with ethyl bromoacetate, the title product is obtained.

EXAMPLE 68:
N-(4,6-dimethylpyrid-2-yl)-6-carboxymethoxy-3,4-dihydro-2,5,7,8-tetramethyl-2H-1-benzopyran-2-thiocarboxamide 1.77 grams (4 mmol) of the compound of Example 67 are dissolved in 40 cm$^3$ of ethanol. 4 cm$^3$ of 2N sodium hydroxide are added dropwise. The mixture is stirred for 2 hours, then the reaction mixture is diluted with 60 cm$^3$ of water and acidified with acetic acid. The mixture is filtered, washed with water and then dried to obtain the title product.

EXAMPLE 69:
N-(4,6-dimethylpyrid-2-yl)-6-ethoxyethoxy-3,4-dihydro-2,5,7,8-tetramethyl-2H-1-benzopyran-2-thiocarboxamide By carrying out the reaction as in Example 66, but replacing the bromomethyl methyl ether of Stage A with bromoethyl ethyl ether, the title product is obtained.

EXAMPLE 70:
N-(4,6-dimethylpyrid-2-yl)-6-ethoxycarbonyloxy-3,4-dihydro-2,5,7,8-tetramethyl-2H-1-benzopyran-2-thiocarboxamide By carrying out the reaction as in Example 66, but replacing the bromomethyl methyl ether of Stage A of Example 66 with ethyl bromoformate, the title product is obtained.

EXAMPLE 71:
N-phenyl-2-(6-acetoxy-3,4-dihydro-2,5,7,8-tetramethyl-2H-1-benzopyran-2-yl)thioacetamide By carrying out the reaction as in Example 1, but replacing 6-hydroxy-3,4-dihydro-2,5,7,8-tetramethyl-2H-1-benzopyran-2-carboxylic acid in Stage A of Example 1 with (6-hydroxy-3,4-dihydro-2,5,7,8-tetramethyl-2H-1-benzopyran-2-yl)acetic acid, the title product is obtained.

EXAMPLE 72:
N-phenyl-6-acetoxy-3,4-dihydro-5,7,8-trimethyl-2H-1-benzopyran-2-thiocarboxamide By carrying out the reaction as in Example 1, but replacing 6-hydroxy-3,4-dihydro-2,5,7,8-tetramethyl-2H-1-benzopyran-2-carboxylic acid in Stage A of Example 1 with 6-hydroxy-3,4-dihydro-5,7,8-trimethyl-2H-1-benzopyran-2-carboxylic acid, the title product is obtained.

EXAMPLE 73:
N-phenyl-6-acetoxy-3,4-dihydro-2-methyl-7-tert-butyl-2H-1-benzopyran-2-thiocarboxamide By carrying out the reaction as in Example 1, but replacing 6-hydroxy-3,4-dihydro-2,5,7,8-tetramethyl-2H-1-benzopyran-2-carboxylic acid in Stage A of Example 1 with 6-hydroxy-3,4-dihydro-2-methyl-7-tert-butyl-2H-1-benzopyran-2-carboxylic acid, the title product is obtained.

EXAMPLE 74:
N-phenyl-6-hydroxy-3,4-dihydro-2-methyl-7-tert-butyl-2H-1-benzopyran-2-thiocarboxamide By carrying out the reaction as in Example 2 (2nd process), but replacing the compound of Example 1 with the compound of Example 73, the title product is obtained.

EXAMPLE 75:
N-phenyl-6-hexanoyloxy-3,4-dihydro-2,5,7,8-tetramethyl-2H-1-benzopyran-2-thiocarboxamide By carrying out the reaction as in Example 1, but replacing the acetic anhydride of Stage A with the chloride of hexanoic acid, the title product is obtained.

EXAMPLE 76:
N-phenyl-6-hydroxy-3,4-dihydro-2,5,7,8-tetramethyl-2H-1-benzopyran-2-thiocarboxamide 3rd Process By carrying out the reaction as in Example 2 (2nd process), but replacing the compound of Example 1 with the compound of Example 75, the title product is obtained.

Melting point: 150°–152° C.

EXAMPLE 77:
N-(2,6-dimethylphenyl)-6-hexanoyloxy-3,4-dihydro-2,5,7,8-tetramethyl-2H-1-benzopyran-2-thiocarboxamide By carrying out the reaction as in Example 1, but replacing the acetic anhydride in Stage A with the chloride of hexanoic acid and the aniline in Stage B with 2,6-dimethylaniline, the title product is obtained.

EXAMPLE 78:
N-(2,6-dimethylphenyl)-6-hydroxy-3,4-dihydro-2,5,7,8-tetramethyl-2H-1-benzopyran-2-thiocarboxamide 3rd Process By carrying out the reaction as in Example 2 (2nd process), but replacing the compound of Example 1 with the compound of Example 77, the title product is obtained.

EXAMPLE 79:
N-(4,6-dimethylpyrid-2-yl)-6-hexanoyloxy-3,4-dihydro-2,5,7,8-tetramethyl-2H-1-benzopyran-2-thiocarboxamide By carrying out the reaction as in Example 1, but replacing the acetic anhydride in Stage A with the chloride of hexanoic acid and the aniline in Stage B with 2-amino-4,6-dimethylpyridine, the title product is obtained.

EXAMPLE 80:
N-(4,6-dimethylpyrid-2-yl)-6-hydroxy-3,4-dihydro-2,5,7,8-tetramethyl-2H-1-benzopyran-2-thiocarboxamide 3rd Process By carrying out the reaction as in Example 2 (2nd process), but replacing the compound of Example 1 with the compound of Example 79, the title product is obtained.

EXAMPLE 81:
N-(3,5-di(tert-butyl)-4-hydroxyphenyl)-6-acetoxy-3,4-dihydro-2,5,7,8-tetramethyl-2H-1-benzopyran-2-thiocarboxamide By carrying out the reaction as in Example 1, but replacing aniline in Stage B with 3,5-di(tert-butyl)-4-hydroxyaniline, the title compound is obtained.

EXAMPLE 82:
N-(3,5-di(tert-butyl)-4-hydroxyphenyl)-6-hydroxy-3,4-dihydro-2,5,7,8-tetramethyl-2H-1-benzopyran-2-thiocarboxamide By carrying out the reaction as in Example 2, but starting from the compound of Example 81, the title compound is obtained.

Melting point: 172°–174° C.

EXAMPLE 83:
1-[(3,4-dihydro-6-acetoxy-2,5,7,8-tetramethyl-2H-1-benzopyran-2-yl)thiocarbonyl]-4-phenylpiperazine Stage A:
1-[(3,4-dihydro-6-acetoxy-2,5,7,8-tetramethyl-2H-1-benzopyran-2-yl)carbonyl]-4-phenylpiperazine 3 g of 6-acetoxy-3,4-dihydro-2,5,7,8-tetramethyl-2H-1-benzopyran-2-carboxylic acid (Stage A, Example 1) are dissolved in 30 cm$^3$ of anhydrous benzene.

3 equivalents (eq) of thionyl chloride are added. The mixture is heated for 6 h at reflux. The mixture is evaporated and the residue is taken up twice in benzene and evaporated. The residue is dissolved in 20 cm$^3$ of dichloroethane. The phenyipiperazine (1.2 eq, i.e. 3.9 cm$^3$) is diluted in 20 cm$^3$ of dichloroethane. Then the solution containing the acid chloride is poured dropwise at ice temperature. The mixture is allowed to return to room temperature. Stirring is continued overnight. The mixture is filtered, evaporated and purified through a column of silica gel, eluting with dichloromethane.

Yield: 77%

Melting point: 112°–113° C.

Stage B:
1-[(3,4-dihydro-6-acetoxy-2,5,7,8-tetramethyl-2H-1-benzopyran-2-yl)thiocarbonyl]-4-phenylpiperazine 2.2 g (5.03 mmol) of the compound obtained in the preceding stage are dissolved in 70 cm$^3$ of anhydrous toluene. 2 g of Lawesson's reagent are added. The mixture is heated for 8 h at reflux. The solvent is evaporated. The residue is purified through a column of silica gel, eluting with dichloromethane. 1.3 g, i.e. a yield of 56%, are isolated.

Melting point: 125°–126° C.

EXAMPLE 84:
1-[(3,4-dihydro-6-hydroxy-2,5,7,8-tetramethyl-2H-1-benzopyran-2-yl)thiocarbonyl]-4-phenylpiperazine 1.1 g of the compound obtained above are dissolved in 50 cm$^3$ of ethanol. Approximately 15 cm$^3$ of a 1N sodium hydroxide solution (7 eq) are added. The mixture is stirred under a nitrogen stream and at room temperature for 2 h. The mixture is diluted in water and acidified with acetic acid diluted by ½. The mixture is filtered. The residue is taken up in dichloromethane and dried over sodium sutfate. The solution is filtered and evaporated.

Yield: 90%

Melting point: 202°–203° C.

Infrared spectral characteristic:
ν (OH): 3435 cm$^{-1}$.

EXAMPLES 85 TO 104

By carrying out the reaction, except when otherwise specified, as in Examples 83 and 84, but using suitably substituted amines, the compounds of the following examples are obtained:

EXAMPLE 85:
1-[(3,4-dihydro-6-acetoxy-2,5,7,8-tetramethyl-2H-1-benzopyran-2-yl)thiocarbonyl]-4-(2-pyridyl)piperazine Yield: 47%
Melting point: 163°-164° C.

EXAMPLE 86:
1-[(3,4-dihydro-6-hydroxy-2,5,7,8-tetramethyl-2H-1-benzopyran-2-yl)thiocarbonyl]-4-(2-pyridyl)piperazine Yield: 91.6%
Melting point: 160°-161° C.
Infrared spectral characteristic:
ν (OH): 3480 cm$^{-1}$.

EXAMPLE 87:
1-[(3,4-dihydro-6-acetoxy-2,5,7,8-tetramethyl-2H-1-benzopyran-2-yl)thiocarbonyl]-4-(4-fluorophenyl)piperazine Yield: 74.1%
Melting point: 134° C.

EXAMPLE 88:
1-[(3,4-dihydro-6-hydroxy-2,5,7,8-tetramethyl-2H-1-benzopyran-2-yl)thiocarbonyl]-4-(4-fluorophenyl)piperazine Yield: 43.7%
Melting point: 141°-142° C.

EXAMPLE 89:
1-[(3,4-dihydro-6-acetoxy-2,5,7,8-tetramethyl-2H-1-benzopyran-2-yl)thiocarbonyl]-4-(4-chlorobenzhydryl)piperazine

EXAMPLE 91:
1-[(3,4-dihydro-6-acetoxy-2,5,7,8-tetramethyl-2H-1-benzopyran-2-yl)thiocarbonyl]-4-(4-chlorophenyl)piperazine

EXAMPLE 92:
1-[(3,4-dihydro-6-hydroxy-2,5,7,8-tetramethyl-2H-1-benzopyran-2-yl)thiocarbonyl]-4-(4-chlorophenyl)piperazine Yield: 39.6%
Melting point: 154°-155° C. (diisopropyl ether)
Infrared spectral characteristic:
ν (OH): 3500 cm$^{-1}$.

EXAMPLE 93:
1-[(3,4-dihydro-6-acetoxy-2,5,7,8-tetramethyl-2H-1-benzopyran-2-yl)thiocarbonyl]-4-(2,3,4-trimethoxybenzyl)piperazine

EXAMPLE 94:
1-[(3,4-dihydro-6-hydroxy-2,5,7,8-tetramethyl-2H-1-benzopyran-2-yl)thiocarbonyl]-4-(2,3,4-trimethoxybenzyl)piperazine Yield: 31.3%
Melting point: 124°-125° C. (diisopropyl ether).

EXAMPLE 95:
1-[(3,4-dihydro-6-acetoxy-2,5,7,8-tetramethyl-2H-1-benzopyran-2-yl)thiocarbonyl]-4-(3,4,5-trimethoxybenzyl)piperazine

EXAMPLE 96:
1-[(3,4-dihydro-6-hydroxy-2,5,7,8-tetramethyl-2H-1-benzopyran-2-yl)thiocarbonyl]-4-(3,4,5-trimethoxybenzyl)piperazine Melting point: 82° C. (isopropyl ether).

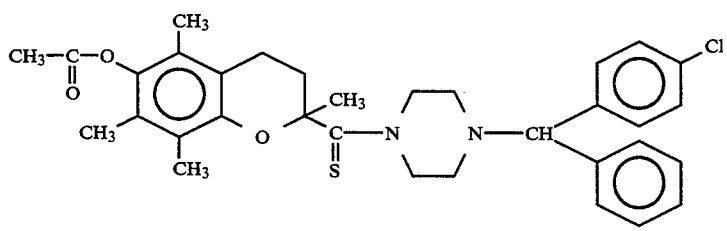

(Example 89)

Yield: 73%
Melting point: 155°-156° C.

EXAMPLE 90:
1-[(3,4-dihydro-6-hydroxy-2,5,7,8-tetramethyl-2H-1-benzopyran-2-yl)thiocarbonyl]-4-(4-chlorobenzhydryl)piperazine Yield: 39%
Melting point: 166°-167° C.

EXAMPLE 97:
1-[(3,4-dihydro-6-acetoxy-2,5,7,8-tetramethyl-2H-1-benzopyran-2-yl)thiocarbonyl]-4-(1-hydroxy-1,1-diphenylmethyl)piperazine

EXAMPLE 98:
1-[(3,4-dihydro-6-hydroxy-2,5,7,8-tetramethyl-2H-1-benzopyran-2-yl)thiocarbonyl]-4-(1-hydroxy-1,1-diphenylmethyl)piperazine

EXAMPLE 99:
1-[(3,4-dihydro-6-acetoxy-2,5,7,8-tetramethyl-2H-1-benzopyran-2-yl)thiocarbonyl]-4-(4,4'-difluorodiphenylmethyl)piperazine

EXAMPLE 100:
1-[(3,4-dihydro-6-hydroxy-2,5,7,8-tetramethyl-2H-1-benzopyran-2-yl)thiocarbonyl]-4-(4,4'-difluorodiphenylmethyl)piperazine Hydrolysis of the acetoxy group: 0.6 g (0.001 mol) of the compound of Example 99 is dissolved in 400 cm³ of methanol. 15 cm³ of potassium hydroxide are added. The mixture is left to stir for 2 h under a nitrogen stream, acidified with 5N hydrochloric acid, and filtered. 0.4 g of a yellow powder is collected.
Yield: 36.2%
Melting point: 204°–205° C.

EXAMPLE 101:
1-[(3,4-dihydro-6-acetoxy-2,5,7,8-tetramethyl-2H-1-benzopyran-2-yl)thiocarbonyl]-4-(4-methoxyphenyl)piperazine

EXAMPLE 102:
1-[(3,4-dihydro-6-hydroxy-2,5,7,8-tetramethyl-2H-1-benzopyran-2-yl)thiocarbonyl]-4-(4-methoxyphenyl)piperazine Melting point: 120°–121° C. (isopropyl ether).

| Elemental analysis: | C | H | N |
|---|---|---|---|
| % theory | 68.13 | 7.32 | 6.35 |
| % found | 67.94 | 7.47 | 6.33 |

EXAMPLE 103:
1-[(3,4-dihydro-6-acetoxy-2,5,7,8-tetramethyl-2H-1-benzopyran-2-yl)thiocarbonyl]-4-(4,6-dimethylpyrid-2-yl)piperazine

EXAMPLE 104:
1-[(3,4-dihydro-6-hydroxy-2,5,7,8-tetramethyl-2H-1-benzopyran-2-yl)thiocarbonyl]-4-(4,6-dimethylpyrid-2-yl)piperazine Melting point: 134° C.

EXAMPLE 105:
1-[(3,4-dihydro-2,5,7,8-tetramethyl-6-trimethylacetoxy-2H-1-benzopyran-2-yl)thiocarbonyl]-4-(4-methoxyphenyl)piperazine Stage A:
1-[(3,4-dihydro-6-hydroxy-2,5,7,8-tetramethyl-2H-1-benzopyran-2-yl)carbonyl]-4-(4-methoxyphenyl)piperazine 5 g (0.017 mol) of 3,4-dihydro-6-hydroxy-2H-1-benzopyran-2-carboxylic acid are dissolved in 150 cm³ of anhydrous tetrahydrofuran (THF). 3 g (1.1 eq, i.e. 0.018 mol) of carbonyldiimidazole (CDI) are added. The mixture is left to stir for 1 h at room temperature. Then 9.5 g (0.034 mol) of 1-(4-methoxyphenyl)piperazine dissolved in 20 cm³ of THF are added. The mixture is left to stir overnight, evaporated and the residue is taken up in dichloromethane. The organic phase is washed with 2N hydrochloric acid, dried over anhydrous sodium sulfate and evaporated. An oil is collected which is crystallized from isopropyl ether.
Yield: 64.38%
Melting point: 149°–150° C. (diisopropyl ether).

Stage B:
1-[(3,4-dihydro-2,5,7,8-tetramethyl-6-trimethylacetoxy-2H-1-benzopyran-2-yl)carbonyl]-4-(4-methoxyphenyl)piperazine 4.4 g (0.01 mol) of the compound obtained in Stage A are dissloved in 75 cm³ of anhydrous pyridine in a round-bottomed flask. 4.99 g (4 eq, i.e. 0.04 mol) of trimethylacetic acid chloride are added dropwise. The mixture is brought to 80° C. and maintained with stirring for 72 h. The mixture is poured onto ice and extracted with ether. The organic phase is washed with water, dried with anhydrous sodium sulfate and evaporated. An oil is obtained which is crystallized from diisopropyl ether.
Yield: 70%
Melting point: 141°–142° C. (diisopropyl ether).

Stage C:
1-[(3,4-dihydro-2,5,7,8-tetramethyl-6-trimethylacetoxy-2H-1-benzopyran-2-yl)thiocarbonyl]-4-(4-methoxyphenyl)piperazine The reaction is carried out as in Stage B of Example 83 to produce the expected compound.
Yield: 64.7%
Melting point: 101°–102° C. (diisopropyl ether).

EXAMPLE 106:
1-[(3,4-dihydro-6-acetoxy-2,5,7,8-tetramethyl-2H-1-benzopyran-2-yl)thiocarbonyl]-4-(1,1-diphenyl-1-acetoxymethyl)piperidine Stage A:
1-[(6-acetoxy-3,4-dihydro-2,5,7,8-tetramethyl-2H-1-benzopyran-2-yl)carbonyl]-4-(1,1-diphenyl-1-hydroxymethyl)piperidine 2.7 g (0.0094 mol) of 3,4-dihydro-6-acetoxy-2H-1-benzopyran-2-carboxylic acid are dissolved in 150 cm³ of anhydrous benzene. 4 cm³ of thionyl chloride are added dropwise. The mixture is left for 4 h at reflux and the solvent is evaporated. The residue is taken up in benzene and then reevaporated. The operation is repeated twice. The oily residue is diluted in 30 cm³ of anhydrous dichloroethane. The acid chloride solution is poured dropwise onto a suspension of 6 g (0.22 mol) of 1,1-diphenyl-1-(4-piperidyl)methanol in 100 cm³ of dichloroethane. The mixture is left to stir overnight, filtered and evaporated. An oil is obtained which is purified on a silica column, eluting with dichloromethane. An oil is collected which is crystallized from diisopropyl ether.
Yield: 77.5%
Melting point: 188°–189° C. (isopropyl ether).

Stage B:
1-[(6-acetoxy-3,4-dihydro-2,5,7,8-tetramethyl-2H-1-benzopyran-2-yl)carbonyl]-4-(1,1-diphenyl-1-acetoxymethyl)piperidine 0.5 g (0.002 mol) of the compound obtained in the preceding stage is poured, at ice temperature, into a solution of 30 cm³ of acetyl chloride. The mixture is left to stir overnight at room temperature and evaporated. The oily residue is taken up in anhydrous benzene, evaporated and an oil is obtained which is purified through a neutral silica column, eiuting with dichloromethane.

Stage C:
1-[(6-acetoxy-3,4-dihydro-2,5,7,8-tetramethyl-2H-1-benzopyran-2-yl)thiocarbonyl]-4-(1,1-diphenyl-1-acetoxymethyl)piperidine 0.3 g (0.72 mmol) of Lawesson's reagent is added to a solution of 400 mg (0.006 mol) of the compound obtained in the preceding stage in 100 cm³ of anhydrous toluene. The mixture is left for 12 h at reflux, evaporated and the oil obtained is purified on a silica column, eluting with dichloromethane. A yellow oil is collected.
Yield: 67%.

EXAMPLE 107:
1-[(3,4-dihydro-6-hydroxy-2,5,7,8-tetramethyl-2H-1-benzopyran-2-yl)thiocarbonyl]-4-(1,1-diphenylmethylidenyl)piperidine 5 cm³ of 1M NaOH are added to a solution in 30 cm³ of ethanol of 0.4 g (0.7 mol) of the compound obtained in Example 106: The mixture is left to stir for 2 h under a nitrogen stream and 50 cm³ of water are added. The mixture is acidified with 2M hydrochloric acid and filtered.
Yield: 83.3%.

EXAMPLE 108: N-phenyl-3,4-dihydro-6-acetoxy-3,5,7,8-tetramethyl-2H-1-benzopyran-2-thiocarboxamide By carrying out the reaction as in Example 1, but replacing 6-hydroxy-3,4-dihydro-2,5,7,8-tetramethyl-2H-1-benzopyran-2-carboxylic acid in Stage A with 6-hydroxy-3,4-dihydro-3,5,7,8-tetramethyl-2H-1-benzopyran-2-carboxylic acid, the title compound is obtained.

EXAMPLE 109:
N-phenyl-3,4-dihydro-6-hydroxy-3,5,7,8-tetramethyl-2H-1-benzopyran-2-thiocarboxamide The title product is obtained by carrying out the reaction as in Example 2 but starting from the compound of Example 108.
Yield: 45%
Melting point: 175° C.

EXAMPLE 110:
1-[(3,4-dihydro-6-acetoxy-2,5,7,8-tetramethyl-2H-1-benzopyran-2-yl)thiocarbonyl]-4-(tert-butoxycarbonyl)piperazine.

Stage A:
1-[(3,4-dihydro-6-acetoxy-2,5,7,8-tetramethyl-2H-1-benzopyran-2-yl)carbonyl]piperazine 2.7 g (0.009 mol) of 3,4-dihydro-6-acetoxy-2,5,7,8-tetramethyl-2H-1-benzopyran-2-carboxylic acid are dissolved in 200 cm³ of anhydrous dichloroethane. 1 eq of carbonyldiimidazole (0.009 mol), i.e. 1.5 g, is added. The mixture is left to stir for 1 h and then 7.5 g of piperazine (0.009 mol) dissolved in 200 cm³ of dichlorcethane are added. The oil obtained after evaporation is purified on a silica column by eluting with a CH₂Cl₂/ethanol/NH₄OH (88/10/2) mixture and crystallized from isopropyl ether.
Yield: 51%.

Stage B:
1-[(3,4-dihydro-6-acetoxy-2,5,7,8-tetramethyl-2H-1-benzopyran-2-yl)carbonyl]4-(tert-butoxycarbonyl)piperazine 1 g (1.1 eq, i.e. 0.004 mol) of di-tert-butylpyrocarbonate is added to a solution of 1.4 g (0.03 mol) of the compound obtained in the preceding stage and 0.75 cm³ of triethylamine in a 50% mixture of water and dioxane. The mixture is left to stir for 2 h as room temperature. Distilled ethyl acetate and water are added. The organic phase is dried with anhydrous sodium sulfate, evaporated and purified on a column, eluting with methylene chloride. A transparent oil is obtained.
Yield: 60%.

Stage C:
1-[(3,4-dihydro-6-acetoxy-2,5,7,8-tetramethyl-2H-1-benzopyran-2-yl)thiocarbonyl]-4-(tert-butoxycarbonyl)piperazine The expected compound is obtained by carrying out the reaction as in Stage B of Example 83.

EXAMPLE 111:
1-[(6-acetoxy-3,4-dihydro-2,5,7,8-tetramethyl-2H-1-benzopyran-2-yl)thiocarbonyl]piperazine 1.1 g of the compound obtained in Example 110 (2.3×10⁻³ mol) are dissolved in 30 cm³ of trifluoroacetic acid. The mixture is left to stir for 2 h, evaporated and the residue is taken up in methylene chloride. 4 cm³ of triethylamine are added. The mixture is stirred for 3 h. The organic phase is washed with water, dried over anhydrous sodium sulfate, evaporated and a yellow glazed substance is obtained.
Yield: 81%

EXAMPLE 112:
1-[(3,4-dihydro-6-hydroxy-2,5,7,8-tetramethyl-2H-1-benzopyran-2-yl)thiocarbonyl]-4-[2,6-di(1-pyrrolidinyl)-4-

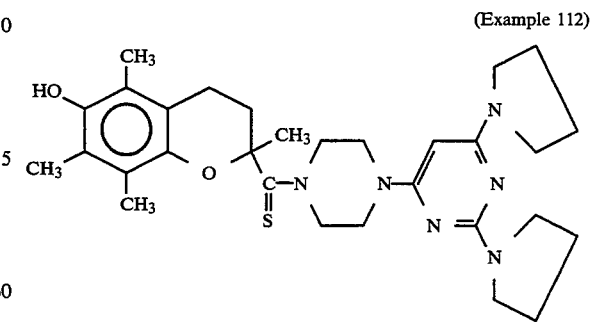
(Example 112)

0.8 g (1.8×10⁻³ mol) of the compound obtained in Example 111 and 1.5 g (5.6×10⁻³ mol) of 4-chloro-2,6-di(1-pyrrolidinyl)pyrimidine are dissolved in 50 cm⁻³ of anhydrous pyridine. The mixture is heated for 2 h at reflux, evaporated and the residue is taken up in dichloromethane. The organic phase is washed with 1N hydrochloric acid and the oil obtained after evaporation is purified on a silica column, eluting with dichloromethane. A yellow oil is collected.

Yield: 25%

Melting point: 168° C.

Infrared spectral characteristic:

$\nu$ (OH): 3440 cm$^{-1}$

EXAMPLES 113 TO 122

By using the processes described above, it is also possible to obtain the compounds of the following examples from suitable starting materials:

EXAMPLE 113: N-phenyl-6-acetoxy-3,4-dihydro-3-ethyl-5,7,8-trimethyl-2H-1-benzopyran-2-thiocarboxamide EXAMPLE 114: N-phenyl-6-hydroxy-3,4-dihydro-3-ethyl-5,7,8-trimethyl-2H-1-benzopyran-2-thiocarboxamide EXAMPLE 115: 1-[(6-acetoxy-3,4-dihydro-3-ethyl-5,7,8-trimethyl-2H-1-benzopyran-2-yl)thiocarbonyl]-4-(4-fluorophenyl)piperazine EXAMPLE 116: 1-[(6-hydroxy-3,4-dihydro-3-ethyl-5,7,8-trimethyl-2H-1-benzopyran-2-yl)thiocarbonyl]-4-(4-fluorophenyl)-piperazine EXAMPLE 117: 1-[(6-acetoxy-3,4-dihydro-7-tert-butyl-2H-1-benzopyran-2-yl)thiocarbonyl]-4-(4-fluorophenyl)piperazine EXAMPLE 118: 1-[(6-hydroxy-3,4-dihydro-7-tert-butyl-2H-1-benzopyran-2-yl)thiocarbonyl]-4-(4-fluorophenyl)piperazine EXAMPLE 119: 1-[(6-acetoxy-3,4-dihydro-5,7,8-trimethyl-2H-1-benzopyran-2-yl)thiocarbonyl]-4-(4-fluorophenyl)piperazine EXAMPLE 120: 1-[(6-hydroxy-3,4-dihydro-5,7,8-trimethyl-2H-1-benzopyran-2-yl)thiocarbonyl]-4-(4-fluorophenyl)piperazine EXAMPLE 121: 1-[(6-acetoxy-3,4-dihydro-3,5,7,8-tetramethyl-2H-1-benzopyran-2-yl)thiocarbonyl]-4-(4-fluorophenyl)piperazine EXAMPLE 122: 1-[(6-hydroxy-3,4-dihydro-3,5,7,8-tetramethyl-2H-1-benzopyran-2-yl) thiocarbonyl]-4-(4-fluoro-phenyl)piperazine EXAMPLE 123: N-(4-guanidino-1-butyl)-3,4-dihydro-6-hydroxy-2,5,7,8-tetramethyl-2H-1-benzopyran-2-thiocarboxamide EXAMPLE 124: ethyl 1-[(3,4-dihydro-6-hydroxy-2,5,7,8-tetramethyl-2H-1-benzopyran-2-yl)thiocarbonyl]-4-hydroxypyrrolidine-2-carboxylate EXAMPLE 125: 1-[(3,4-dihydro-6-hydroxy-2,5,7,8-tetramethyl-2H-1-benzopyran-2-yl)thiocarbonyl]-4-hydroxypyrrolidine-2-carboxylic acid PHARMACOLOGICAL STUDY OF THE COMPOUNDS OF THE INVENTION (The compounds are compared with the closest compound of the prior art which is Example 102 of Application WO 88/08424)

Example A: Study of the Antiperoxidizing Activity

The action of the compounds of the invention, which are capable of trapping .OH radicals, was studied, on the one hand, on the spontaneous peroxidation of lipids and, on the other hand, on the peroxidation induced by the $Fe^{2+}$/ascorbate (10 $\mu$m/250 $\mu$m) system on rat brain homogenates.

During the measurement of the spontaneous lipid peroxidation, the rat brain homogenates are placed in the presence or in the absence of the compounds to be tested for 60 minutes at 37° C. The reaction is halted at 0° C. and the quantitative determination of malondialdehyde is carried out using thiobarbituric acid by the method of Yagi, K., (1976), Blochem. Med., 15, 212–216. Lipid peroxidation is determined by the substances reacting with thiobarbituric acid expressed in nanomoies of malondialdehyde.

During the measurement of the induced lipid peroxidation, the methodology is identical to the above with the exception of the addition to the homogenate of the radical inductive system: $Fe^{2+}$/ascorbate. The reference substances are probucol and vitamin E.

The concentrations of the tested compounds which inhibit by 50% the peroxidation of the substrate or the antioxidizing activity of the compounds of the invention at a concentration of $10^{-5}M$ are calculated.

It appears that certain compounds of the invention have a particularly intense antiperoxidizing activity which is greater by a factor of 100 than that of the closest compound of the prior art. This very advantageous result occurs whether the peroxidation is spontaneous or induced by a chemical system.

TABLE A

STUDY OF THE ANTIPEROXIDIZING ACTIVITY OF THE COMPOUNDS OF THE INVENTION AT $10^{-5}$ M

| Compound (EXAMPLE No.) | INHIBITION OF THE PEROXIDATION WITH RESPECT TO THE CONTROL | |
|---|---|---|
|  | SPONTANEOUS PEROXIDATION | INDUCED PEROXIDATION |
| 2 | 100 | 100 |
| 4 | 98 | 100 |
| 26 | 99 | 100 |

Example B: Study of the Ability to Protect LDLs From Oxidation

The capacity of the compounds of the invention to reduce the proportions of oxidized LDLs was measured in the following way. A 24-hour incubation combining native LDLs, a $Cu^{2+}$ system generating free radicals and the compounds to be tested is carried out.

The results are obtained after analysis of the medium by a high performance chromatographic technique: FPLC (Fast Protein Liquid Chromatography). The protective ability of the tested compound is determined after comparison of the chromatogram obtained with that of the positive reference control: probucol.

It is clearly apparent that the compounds of the invention have a very significant protective ability and one which is significantly greater than that of the closest compound of the prior art.

Example C: Study of the Inhibitory Activity of the Compounds of Formula (I) Used According to the Invention on the Synthesis of Eicosanoids 1) Study of the Inhibitory Acivity on the Synthesis of Eicosanoids Resulting from Cyclooxygenase The aim of this study is to measure the inhibitory activity of the molecules used according to the invention on the secretion of prostaglandin $E_2$ ($PGE_2$), one of the main eicosanoids produced by the cyclooxygenase of human granulocytes stimulated by the calcium ionophore A23187.

PROTOCOL

Isolation of human granulocytes:

Human venous blood from blood donors who have not taken medicaments for 2 weeks is withdrawn into polypropylene tubes containing 1 volume of anti-coagulant (2.73% citric acid, 4.48% sodium citrate, 2% glucose) per 10 volumes of blood.

In the hour following the withdrawal, 6% dextran is added to the blood (0.3 $cm^3/cm^3$ of blood). After incubating for 30 min at 37° C., the plasma which is rich in white corpuscles is centrifuged at a speed of 100 g for 5 min at 4° C.

The button is resuspended in 3 $cm^3$ of 0.83% $NH_4Cl$ (to lyse the contaminating red corpuscles) and centrifuged at a speed of 100 g for 5 min at 4° C.

The button which is rich in mono- and polynucleated white corpuscles is recovered in 5 $cm^3$ of phosphate buffer (pH 7.4) having the following composition (in mM): 137 NaCl, 2.68 KCl, 8.1 $Na_2HPO_4$, 1.47 $KH_2PO_4$, 0.9 $CaCl_2$, 0.5 $MgCl_2$ and deposited on 3 $cm^3$ of a Ficoll Type 400 solution at a density of 1.077.

After centrifuging at a speed of 420 g for 30 min at 4° C., the button which is rich in granulocytes is resuspended in 5 $cm^3$ of phosphate buffer and centrifuged at a speed of 100 g, 5 min at 4° C. Finally, the granulocytes are counted and the density is adjusted to $3 \times 10^6$ cells/$cm^3$ of phosphate buffer.

Stimulation of the granulocytes with the calcium ionophore A23187:

The cells ($3 \times 10^6$ cells/$cm^3$) are preincubated at 37° C. for 15 min in the absence or in the presence of the products to be tested at the desired concentration. The cells are then stimulated for 15 min at 37° C. with A23187 at $5 \times 10^{-6}M$ (mother solution at $10^{-2}M$ in DMSO). The base level is measured from cells which receive neither products to be tested nor A23187.

The reaction is terminated in ice and the supernatant is recovered after centrifuging at a speed of 250 g for 5 min at 4° C.

Quantitative determination of $PGE_2$:

The amount of $PGE_2$ produced is measured by a radioimmunological test (RIA). A calibration range is produced under the same conditions with common concentrations of $PGE_2$.

Results:

The compounds of formula (I) used according to the invention show an inhibitory activity on the synthesis of eicosonoids resulting from cyclooxygenase which is much greater than that of probucol.

2) Study of the Inhibitory Activity on the Synthesis of Eicosanoids Resulting From Lipoxygenase The inhibitory activity of the compounds of formula (I) used according to the invention on the synthesis of eicosanoids is measured on washed human polynuclear cells, in the presence or in the absence of the compound to be tested, after activation of these cells by calcium (calcium ionophore A23187).

The production of the main eicosanoid, resulting from lipoxygenase, produced by human polynuclear cells: leukotriene $B_4$ ($LTB_4$), is measured by a radioimmunological test.

The compounds of formula (I) used according to the invention show an inhibitory activity on the synthesis of eicosanoids resulting from the lipoxygenase which is much greater than that of probucol.

TABLE B

INHIBITORY ACTIVITY OF THE COMPOUNDS OF THE INVENTION ON THE BIOSYNTHESIS OF EICOSONOIDS RESULTING FROM LIPOXYGENASE

| | INHIBITION OF THE SYNTHESIS OF LTB$_4$ | |
|---|---|---|
| Compound (EXAMPLE No.) | % OF INHIBITION AT $10^{-5}$ M | CONCENTRATION INHIBITING SYNTHESIS BY 50% (IC$_{50}$ in M) |
| 2 | >99% | 0.3 |
| 4 | >99% | 0.5 |
| 6 | >99% | 0.6 |
| 8 | >99% | |
| 26 | >99% | 0.5 |
| 84 | >99% | 0.3 |
| 86 | >99% | 0.2 |
| 88 | >99% | 0.1 |
| 92 | >99% | 0.2 |
| 94 | >99% | 0.3 |
| 98 | >99% | 1.3 |

CONCLUSION

Studies 1 and 2 of Example C show that the compounds used according to the invention have an intense inhibitory activity on the synthesis of eicosanoids.

Example D: Study of the Protective Ability of the Compounds of the Invention on Intracellular pH The protective ability on the intracellular pH of the compounds of the invention was tested on the Cl$^-$/HCO$_3^-$ carriers (intracellular pH regulators) of cultured cardiocytes.

METHOD

Cultured cardiocytes (Eur. J. Pharmacol., 1991, Vol. 205, pp 29-34)

Cells:

We have used a line of rat cardiac myoblasts (H$_9$C$_2$), marketed by ATCC (Rockville, Md., USA). In these cells, the unidirectional departure of bicarbonate is catalyzed mostly by the sodium-independent Cl$^-$/HCO$_3^-$ exchanger and the unidirectional entry of bicarbonate is catalyzed, mostly, by the bicarbonate carrier coupled to extracellular Na$^+$ (sodium-dependent Cl$^-$/HCO$_3^-$ exchanger). The concomitant variations in intracellular pH can be followed by spectrofluorimetry. The cells were cultured in 75 cm$^2$ culture flasks. At each passage, the cells were detached by treatment with trypsin. The cells were taken up again with an ad hoc volume of fresh culture medium and inoculated on 3.15 cm$^2$ sterile cover glasses. The cells are used at confluence, from 1 to 2 days later.

Determination of intracellular pH using BCECF (2',7'-bis(carboxyethyl)-5(6)-carboxyfluorescein):

We have used a molecule derived from fluorescein, BCECF, whose fluorescence depends on its protonation state: this molecule has the distinctive characteristic of fluorescing at 525 nm, after having been excited at 508 nm, all the less so because the pH is low.

The fluorescence of BCECF is calibrated, in terms of intracellular pH, in a medium whose K$^+$ concentration is equal to the intracellular K$^+$ concentration and in the presence of 10 $\mu$M of nigericin (ionophore which exchanges K$^+$ for H$^+$ and which provides that the intra- and extracellular pHs are equal). Known and increasing amounts of 1M MOPS acid (4-morpholinopropanesulfonic acid) are added to the medium and the resulting pH and fluorescence are measured.

BCECF Charge:

After withdrawal of the initial culture medium, and two washings with Ringer medium, the cover glasses are incubated in 1 cm$^3$ of Ringer medium containing BCECF-AM, the esterified form at 37° C. The Ringer medium has the following composition (mM): NaCl 145, KCl 5, MgCl$_2$ 1, CaCl$_2$ 1, MOPS-TRIS 10 (pH 7.4), glucose 5. The medium is then replaced with Ringer medium which does not contain BCECF-AM and the cells are incubated for 10 minutes at 37° C. in order to make possible better deesterification of the label. Finally, the cells are incubated for 10 minutes at room temperature (25° C.), either in Ringer medium or in a similar medium (Bicarbonate medium) where 25 mM of Na$^+$Cl$^-$ were substituted by 25 mM of Na$^+$HCO$_3^-$ (at constant pH). This last stage makes it possible for the cells to adapt to the experimental temperature. If appropriate, it makes it possible for the cytosolic pH to equilibrate as a function of the bicarbonate. In order to determine the entry of bicarbonate, the cells are preincubated in the absence of bicarbonate and the experimental measurements are carried out in the presence of bicarbonate (bicarbonate entry stage=alkalinization). Conversely, in order to determine the departure of bicarbonate, the cells are preincubated in the presence of bicarbonate and the experimental measurements are carried out in the absence of bicarbonate (bicarbonate departure stage=acidification). It is to be noted that the experiments relating to departure of bicarbonate are carried out in the presence of 2 mM of amiloride intended to reduce the pH balancings which are produced when the [Na$^+$/H$^+$] exchanger is activated.

Measurement of the fluorescence:

The cover glasses are arranged vertically on a carrier which is placed in a fluorimetry tank containing 2 cm$^3$ of experimental medium (Ringer medium or Bicarbonate medium). The fluorescence is measured at 525 nm, after excitation at 508 nm, on a Shimadzu RF 5000 spectrofluorimeter. The excitation and emission slits are 5 nm.

The measurements are carried out at room temperature (25° C.) every 2 seconds. A standard experiment (one cover glass) lasts approximately 15 minutes. If appropriate, the calibration is carried out at the end of the experiment, by passing into K$^+$ medium with nigericin and successive additions of acid aliquots (5 $\mu$l of 1M MOPS in a volume of 2 cm$^3$).

In these experiments, the self-fluorescence of the cells and the background noise are negligible (<1% of the total signal, i.e. a signal/noise ratio>100).

RESULTS

The results of this study show that the compounds of the invention are very powerful inhibitors of the departure of bicarbonate from cardiocytes. The departure of bicarbonate from cardiocytes is catalyzed by the sodium-independent Cl$^-$/HCO$_3$— exchanger and not by that which is dependent on sodium. On the other hand, it appears that the compounds of the invention are very poor inhibitors of the entry of bicarbonate, which is essentially catalyzed by the sodium-dependent Cl$^-$/HCO$_3^-$ exchanger.

In conclusion, the compounds of the invention are powerful inhibitors of the sodium-independent Cl$^-$/HCO$_3^-$ exchanger, a property which translates into a cell retention of bicarbonate. In ischemiated tissue, this is advantageous for neutralizing cell acidification and the ionic and metabolic traumas associated with this acidification.

Example E: Study of the Acute Toxicity

The acute toxicity was assessed after oral administration to batches of 3 mice (20±2 grams) of increasing doses (0.1/0.25/0.50/0.75/1 g/kg) of compounds of formula (I). The animals were observed at regular intervals during the first day and daily for the 2 weeks following the treatment.

It appears that the compounds of formula (I) are entirely non-toxic. No mortality was observed after administrating a dose of 1 g.kg$^{-1}$. Disorders are not observed after administrating this dose.

Example F: Pharmaceutical Composition: Tablets

Tablets containing a dose of 10 mg of N-phenyl-6-hydroxy-3,4-dihydro-2,5,7,8-tetramethyl-2H-1-benzopyran-2-thiocarboxamide

| Formula for the preparation of 1000 tablets: | |
|---|---|
| N-phenyl-6-hydroxy-3,4-dihydro-2,5,7,8-tetramethyl-2H-1-benzopyran-2-thiocarboxamide | 10 g |
| Wheat starch | 15 g |
| Maize starch | 15 g |
| Lactose | 65 g |
| Magnesium stearate | 2 g |
| Silica | 1 g |
| Hydroxypropylcellulose | 2 g |

We claim:

1. A compound selected from those of formula (I):

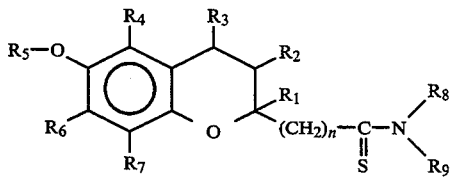

in which:
n is 0 or 1, $R_1$, $R_2$, $R_3$, $R_4$, $R_6$ and $R_7$, which are identical or different, each represents independently of one another hydrogen or lower alkyl $R_a$—, where $R_a$ represents a linear or branched alkyl group having 1 to 8 carbon atoms, inclusive,
$R_5$ represents:
hydrogen,
lower alkyl $R_a$—,
lower acyl $R_a$—CO—,
alkoxyalkyl of formula $R_a$—O—$R_b$—,
alkoxycarbonyl of formula $R_a$—O—CO—,
alkoxycarbonylalkyl of formuls $R_a$—O—CO—$R_b$—,
carboxyalkyl of formula HOOC—$R_a$—, where $R_a$ and $R_b$, which are identical or different, each represent, independently of one another, a linear or branched alkyl radical having 1 to 8 carbon atoms, inclusive,
$R_8$ and $R_9$
form, together with the nitrogen atom which carries them, a group chosen from:
piperazine and
substituted piperazine,
it being understood that the term "substituted" as applied to the above piperazine, and groups, means that it can be substituted by one or a number of halogen, hydroxyl, carboxyl, or $R_{10}$ radicals, with $R_{10}$ being chosen from:
alkyl,
alkoxy,
alkenyl,
—$(CH_2)_n$—$R_{11}$, where n represents 0 or an integer from 1 to 5 inclusive and where $R_{11}$ represents a radical chosen from phenyl, benzhydryl, 1,1-diphenylmethylidenyl, pyrimidinyl, and pyridyl, it being possible for these radicals $R_{10}$ themselves to be substituted by halogen, trifluoromethyl, oxo, carboxyl, hydroxyl, atkyl, alkoxy, haioalkoxy, acetyl, or pyrrolidinyl, its optical isomers, in the pure form or in the form of mixtures, and addition salts thereof with a pharmaceutically-acceptable acid or base.

2. A compound according to claim 1, selected from those in which $R_5$ represents hydrogen, its optical isomers, and addition salts thereof with a pharmaceutically-acceptable acid or base.

3. A compound according to claim 1, which is selected from 1-[(3,4-dihydro-6-hydroxy-2,5,7,8-tetramethyl-2H-1-benzopyran-2-yl)thiocarbonyl]-4-(4-chlorobenzhydryl)piperazine, an optical isomer thereof, and an addition salt thereof with a pharmaceutically-acceptable acid or base.

4. A compound according to claim 1, which is selected from 1-[(3,4-dihydro-6-hydroxy-2,5,7,8-tetramethyl-2H-1-benzopyran-2-yl)thiocarbonyl]-4-(4-fluorophenyl)piperazine, an optical isomer thereof, and an addition salt thereof with a pharmaceutically-acceptable acid or base.

5. A pharmaceutical composition useful in combating a disorder connected with the biosynthesis of eicosanoids containing a compound as claimed in claim 1 in combination with a pharmacologically-acceptable excipient.

6. A method of treating a mammal afflicted with a disorder connected with biosynthesis of eicosanoids comprising the step of administering to the said mammal an amount of a compound according to claim 1 which is effective for alleviation of said disorder.

7. A method of treating according to claim 6 wherein the disorder is an inflammatory diseases.

* * * * *

UNITED STATES PATENT AND TRADEMARK OFFICE
CERTIFICATE OF CORRECTION

PATENT NO. : 5,395,834
DATED : March 7, 1995
INVENTOR(S) : Guillaume LeBaut, Jean-Paul Babingui, Sylvie Robert-Piessard, Pierre Renard, Daniel-Henri Caignard, Jean-Francois Renaud de la Faverie, Gèrard Adam It is certified that error appears in the above-indentified patent and that said Letters Patent is hereby corrected as shown below:

TITLE PAGE, ITEM [56] FOREIGN PATENT DOCUMENTS; "505017 9/1972 European Pat. Off. ." should read -- 504017 9/1972 European Pat. Off. . --

Column 1, line 6; insert at the end of the line -- ,now USP 5,393,775 --

Column 2, line 1; inert at the end of the line "CO-$R_b$-," to make it read -- $R_a$-O-CO-$R_b$-, --

Column 2, line 2; delete "CO-$R_b$-," at the beginning of the line.

Column 2, line 39; delete "-N-" at the end of the line.

Column 2, line 40; insert "-N" at the beginning of the line to make it read -- -NH-($CH_2$)$_k$-$NH_2$ --

Column 3, line 13; insert at the end of the line ")$_m$-" to make it read -- A-($CH_2$)$_m$- --

Column 3, line 14; delete the ")$_m$-" at the beginning of the line.

Column 3, line 23; delete the "$R_a$-O- -" at the end of the line.

Column 3, line 24; insert at the beginning of the line "$R_a$-O-" to make it read -- $R_a$-O-CO-$R_b$- --

Column 3, line 27; insert ")$_q$-," at the end of the line to make it read -- B-($CH_2$)$_q$- --

Column 3, line 28; delete the ")$_q$-," at the beginning of the line.

Column 3, line 31; insert ")$_q$-," at the end of the line to make it read -- E-($CH_2$)$_q$-, --

Column 3, line 32; delete the ")$_q$-," at the beginning of the line.

Column 3, line 35; insert ")$_q$-," at the end of the line to make it read -- ($CH_2$)$_q$-, --

Column 3, line 36; delete the ")$_q$-," at the beginning of the line.

Column 3, line 41; "quinoiine" should read -- quinoline --

UNITED STATES PATENT AND TRADEMARK OFFICE
CERTIFICATE OF CORRECTION

PATENT NO. : 5,395,834
DATED : March 7, 1995
INVENTOR(S) : Guillaume Le Baut, Jean-Paul Babingui, Sylvie Robert-Piessard, Pierre Renard, Daniel-Henri Caignard, Jean-Francois Renaud de la Faverie, Gèrard Adam It is certified that error appears in the above-indentified patent and that said Letters Patent is hereby corrected as shown below:

Column 4, line 55; insert at the end of the line "Hal" to make it read -- $R_5''$-Hal --
Column 4, line 56; delete "Hal" at the beginning of the line.
Column 5, line 43; insert "CO-," at the end of the line to make it read -- $R_a$-CO-, --
Column 5, line 44; delete "CO-," at the beginning of the line.
Column 11, line 66; "Exampls" should read -- Example --
Column 12, line 9; "4" should read -- 24 --
Column 15, line 63; "tetr-methyl" should read -- tetramethyl --
Column 19, line 36; "dimethylaniiine" should read -- dimethylaniline --
Column 20, line 33; "phenyipiperazine" should read --phenylpiperazine --
Column 20, line 64; "dichioromethane" should read -- dichloromethane --
Column 20, line 65; "sutfate" should read -- sulfate --
Column 25, line 39; insert "108:" after "EXAMPLE"
Column 25, line 40; delete "108:" at the beginning of the line.
Column 26, line 2; "dichlorcethane" should read -- dichloroethane --
Column 26, line 17; "as room" should read -- at room --
Column 26, line 47; insert after "-4-" -- pyrimidinyl] piperzine --
Column 29, line 6; "nanomoies" should read -- nanomoles --
Column 30, line 25; "$3x10^6$" should read -- $3x10^{-6}$ --
Column 30, line 29; "($3x10^6$" should read -- ($3x10^{-6}$ --
Column 31, line 4; "EICOSONOIDS" should read --EICOSANOIDS--.

UNITED STATES PATENT AND TRADEMARK OFFICE
CERTIFICATE OF CORRECTION

PATENT NO. : 5,395,834

DATED : March 7, 1995

INVENTOR(S) : Guillaume Le Baut, Jean-Paul Babingui, Sylvie Robert-Piessard, Pierre Renard, Daniel-Henri Caignard, Jean-Francois Renaud de la Faverie, Gèrard Adam It is certified that error appears in the above-indentified patent and that said Letters Patent is hereby corrected as shown below:

Column 33, line 55; "formuls" should read -- formula --.
Column 34, line 10; delete ",and".
Column 34, line 23; "haioalkoxy" should read -- haloalkoxy --.
Column 34, line 56; "diseases" should read -- disease --.

Column 34, line 23, "atkyl" should read --alkyl -.

Signed and Sealed this

Fourth Day of July, 1995

Attest:

BRUCE LEHMAN

Attesting Officer

Commissioner of Patents and Trademarks